United States Patent
Wang et al.

(10) Patent No.: US 12,195,742 B2
(45) Date of Patent: Jan. 14, 2025

(54) MAIZE ZmHsf21 GENE AND USE THEREOF

(71) Applicant: CHINA AGRICULTURAL UNIVERSITY, Beijing (CN)

(72) Inventors: Xi-Qing Wang, Beijing (CN); Weiwei Jin, Beijing (CN); Wei Huang, Beijing (CN); Junhong Zhuang, Beijing (CN); Yunfei Li, Beijing (CN); Lingling Pan, Beijing (CN); Xiaoming Zhao, Beijing (CN); Fang Liu, Beijing (CN)

(73) Assignee: CHINA AGRICULTURAL UNIVERSITY, Beijing (CN)

( * ) Notice: Subject to any disclaimer, the term of this patent is extended or adjusted under 35 U.S.C. 154(b) by 0 days.

(21) Appl. No.: 17/636,569

(22) PCT Filed: Aug. 3, 2020

(86) PCT No.: PCT/CN2020/106580
§ 371 (c)(1),
(2) Date: Feb. 18, 2022

(87) PCT Pub. No.: WO2021/031834
PCT Pub. Date: Feb. 25, 2021

(65) Prior Publication Data
US 2022/0282272 A1    Sep. 8, 2022

(30) Foreign Application Priority Data

Aug. 21, 2019  (CN) ......................... 201910775329.8

(51) Int. Cl.
*C12N 15/82* (2006.01)
*C07K 14/415* (2006.01)
(52) U.S. Cl.
CPC ........ *C12N 15/8282* (2013.01); *C07K 14/415* (2013.01)
(58) Field of Classification Search
None
See application file for complete search history.

(56) References Cited

U.S. PATENT DOCUMENTS

2017/0114356 A1*  4/2017  Li ........................ C07K 14/415

FOREIGN PATENT DOCUMENTS

| CN | 102264907 A | 11/2011 |
| CN | 104232679 A | 12/2014 |
| CN | 104558128 A | 4/2015 |
| CN | 109369789 A | 2/2019 |

OTHER PUBLICATIONS

Guo et al., 2004, Proc. Natl. Acad. Sci. USA 101: 9205-9210 (Year: 2004).*
Jiang et al., Acta Physiologiae Plantarum 40 (2018): 1-12 (Year: 2017).*
GenBank Accession NM_001153656.2 https://www.ncbi.nlm.nih.gov/nuccore/NM_001153656.2; available Nov. 20, 2009. (Year: 2009).*
GenBank Accession NM_001371965.1 https://www.ncbi.nlm.nih.gov/nuccore/NM_001371965.1 available Jun. 26, 2021 (Year: 2021).*
Haider et al., Agronomy 11.11 (2021): 2335; Abstract, Figures 5-6, 8 (Year: 2021).*
Lin et al., BMC genomics 12 (2011): 1-14 (Year: 2011).*
Alexandrov et al., 2009, Plant Mol Bio, 69:179-194.*
Sun et al, 2018, Bio-Protocol, 8:1-9.*
Campos-Bermudez et al., 2013, PLOS ONE, 8:1-10.*
Al-Whaibi, 2011, Journal of King Saud University, 23:139-150.*
GenBank Accession No. EU966517, *Zea mays* clone 294971 heat shock factor Protein 4 mRNA, complete cds. 2 pages, Dec. 10, 2008.
GenBank Accession No. NM_001371965, *Zea mays* uncharacterized LOC100283948 (LOC100283948), mRNA. 2 pages, Jun. 26, 2021.
International Search Report and Written Opinion for Application No. PCT/CN2020/106580, dated Nov. 9, 2020, 9 pages.

* cited by examiner

Primary Examiner — Jason Deveau Rosen
(74) Attorney, Agent, or Firm — McCarter & English, LLP; Wei Song; Miao Yu

(57) ABSTRACT

The present invention provides a ZmHsf21 gene, a protein encoded thereby and use thereof in plant breeding. In particular, the present invention provides use of the ZmHsf21 gene in increasing plant yield and improving plant disease-resistance, especially stalk rot.

10 Claims, 4 Drawing Sheets

Specification includes a Sequence Listing.

SEQUENCE LISTING

```
<160> NUMBER OF SEQ ID NOS: 13

<210> SEQ ID NO 1
<211> LENGTH: 1535
<212> TYPE: DNA
<213> ORGANISM: maize

<400> SEQUENCE: 1
cggccatcac gacgacgcca gggcggagag ctagccggcc ggagcccaca cgcagctgga      60
agcaccagat caccgatcgt gccggccgag cggcggcgca ggcgcacagg cgcttacatg     120
ggagtagagg cgggcgggtg cgggcggagg gcggtcgtca ccgggttcta cgtctgggc     180 tgggagttcc tcaccgccct ccttctcttc tcggccgccg tcgccgccgc agactcctac     240
tagcaagcta cctaccttct ttctttcatt cccttaggta gctcagccgt acacacaaca     300
gcacacaagt catcagttac tagctagtta gtagcctata caacacatac atatatacat     360
acaaaggtga gtgaggttcg cgtgcaagca gagccaatcg tgccgatcga gctatataca     420 tagccggcg cgagagatgg gagaagcggc ctcgccgtg gcggcgtcga agaggggcgg     480
cggcgggccg gcgccgttcc tgaccaagac gcaccagatg gtggaggagc ggggcacgga     540
cgaggtgatc tcgtgggcgg agcagggccg ctccttcgtg gtgtggaagc ccgttgagct     600
ggcgcgcgac ctcctcccgc tccacttcaa gcactgcaac ttctcctcct tcgtccgcca     660
gctcaacacc tacggtttcc ggaaggtggt gccggaccgg tgggagttcg cgaacgacaa     720
cttccgtcga ggcgagcagg gtctcctgtc cggcatccgc cgccgcaagt caacggcgct     780
gcagatgtcc aagtccggat ccggcggcag cggcggcgtg aacgccacgt tcccccgcc     840 tctgcccct ccacctcccg cgtcggccac cacgtccggc gtccacgagc gcagctcgtc     900
```

```
gtcggcgtcg tcgccaccgc gggcgcccga cctggccagc gagaacgagc agctcaagaa    960
ggacaaccac acgctgtccg tcagctggcg caggcgcgc cggcactgcg aggagctcct    1020
gggcttcctc tcgcgcttcc tcgacgtccg gcagctcgac ctccggctgc tcatgcagga    1080
ggacgtgcga gcggggcaa gcgacgacg cgcacagcgc cgcgcgcacg cagtggccag    1140
ccagctggag cgcggcggcg gcgaggaggg gaagagcgtg aagctgttcg gcgtactctt    1200
aaaggacgcc gcgaggaaga ggggccggtg cgaggaagcg gcggcagcg agcggcccat    1260
caagatgatc agggtcggcg agccgtgggt cggcgtcccg tcgtcgggcc cgggccggtg    1320
cggcggcgag aattaactgt catccaatgt gaggttgatg acaaggacag tttcatccat    1380
catatcgagc aagtaacaaa gccagtgctg tggtaaaact gcaaagacag aacacaggac    1440
acaggagaaa tataggcgta agcatgttaa ttaagaatta attatatatg ggatgctttt    1500
gaagtgaaaa aaaaaaaaaa aacatgtacg ggcca                              1535

<210> SEQ ID NO 2
<211> LENGTH: 1671
<212> TYPE: DNA
<213> ORGANISM: maize

<400> SEQUENCE: 2
aggcgatgag cgcctctcgc gacgccaggg cggagagcta gccggccggg agcccacacg      60
cagctggaag caccagaccg atcgtgccgg ccgagcggcg cgcaggcgc aggcgcttac     120
atgggagtag aggcgggcgg gtgcgggcgg agggcggtcg tcaccgggtt ctacgtctgg     180
ggctgggagt tcctcaccgc cctccttctc ttctcggccg ccgtcgccgc cgcagactcc     240
tactagcaag ctaccaacct tctttctttc attcccttag gtagctcagc cgtacacaca     300
acaacacaca agtcatcagt tactagctag ttagtagcct atacaacaca tacatacata     360
caaaggtgag tgaggttcgc gtgcaagcag agccaatcgt gccgatcgag ctatatacat     420
agccggcggc gagggatggg agaagcgccc gcggccgtgg cggcgtcgaa gagggcggc    480
gggccggcgc cgttcctgac caagacgcac cagatggtgg aggagcgggg cacggacgag    540
gtgatctcgt gggcggagca gggccgctcc ttcgtggtgt ggaagcccgt ggagctggcg    600
cgcgacctcc tcccgctcca cttcaagcac tgcaacttct cctccttcgt ccgccagctc    660
aacacctacg gtttccgaaa ggtggtgccg gaccggtggg agttcgcgaa cgacaacttc    720
cgtcgaggcg agcagggtct cctgtccggc atccgccgcc gcaagtcaac ggcgctgcag    780
atgtccaagt ccggatccgg cggcagcggc ggcgtgaacg ccacgttccc cccgcctctg    840
ccccctccgc ctcccgcgtc ggccaccacg tccggcgtcc acgagcgcag ctcgtcgtcg    900
gcgtcgtcgc caccgcgggc gcccgacctg ccagcgagaa acgagcagct caagaaggac    960
aaccacacgc tgtccgccga gctggcgcag gcgcgccggc actgcgagga gctcctgggc   1020
ttcctctcgc gcttcctcga cgtccggcag ctcgacctcc ggctgctcat gcaggaggac   1080
gtgcgagcg gggcaagcga cgacggcgca cagcgccgcg cacgcagt ggccagccag   1140
ctggagcgcg gcggcggcga ggaggggaag agcgtgaagc tgttcggcgt actcttaaag   1200
gacgccgcga ggaagagggg ccggtgcgag gaagcggcgg ccagcgagcg gcccatcaag   1260
atgatcaggg tcggcgagcc gtgggtcggc gtcccgtcgt cgggcccggg ccggtgcggc   1320
ggcgagaatt aactgtcatc caatgtgagg ttgatgacaa ggacagtttc atccatcata   1380
tcgagcaagt aacaaagcca gtgctgtggt aaaactgcaa agacagaaca caggacacag   1440
gagaaatata ggcgtaagca tgttaattaa gaattaatta tatatgggat gcttttgaag   1500
```

```
tagcaagatt ggaagtagag ataagtaaaa cgggctagaa gcagcgccca tgtgttcaga    1560
atggaaaatt agcgtttccg tgtgtgtgtt aagaaaaact tatatgcgct ttctgcgagc    1620
acggttgatt cttaagagcg acagcaaatg aaaggtgtat tattaattga a             1671

<210> SEQ ID NO 3
<211> LENGTH: 900
<212> TYPE: DNA
<213> ORGANISM: maize

<400> SEQUENCE: 3
atgggagaag cggcctcggc cgtggcggcg tcgaagaggg gcggcggcgg gccggcgccg      60
ttcctgacca agacgcacca gatggtggag gagcggggca cggacgaggt gatctcgtgg     120
gcggagcagg gccgctcctt cgtggtgtgg aagcccgttg agctggcgcg cgacctcctc     180
ccgctccact tcaagcactg caacttctcc tccttcgtcc gccagctcaa cacctacggt     240
ttccggaagg tggtgccgga ccggtgggag ttcgcgaacg acaacttccg tcgaggcgag     300
cagggtctcc tgtccggcat ccgccgccgc aagtcaacgg cgctgcagat gtccaagtcc     360
ggatccggcg gcagcggcgg cgtgaacgcc acgttccccc cgcctctgcc ccctccacct     420
cccgcgtcgg ccaccacgtc cggcgtccac gagcgcagct cgtcgtcggc gtcgtcgcca     480
ccgcgggcgc ccgacctggc cagcgagaac gagcagctca agaaggacaa ccacacgctg     540
tccgtcgagc tggcgcaggc gcgccggcac tgcgaggagc tcctgggctt cctctcgcgc     600
ttcctcgacg tccggcagct cgacctccgg ctgctcatgc aggaggacgt gcagcggggg     660
gcaagcgacg acggcgcaca gcgccgcgcg cacgcagtgg ccagccagct ggagcgcggc     720
ggcggcgagg aggggaagag cgtgaagctg ttcggcgtac tcttaaagga cgccgcgagg     780
aagaggggcc ggtgcgagga agcggcggcc agcgagcggc ccatcaagat gatcagggtc     840
ggcgagccgt gggtcggcgt cccgtcgtcg ggcccgggcc ggtgcggcgg cgagaattaa     900

<210> SEQ ID NO 4
<211> LENGTH: 897
<212> TYPE: DNA
<213> ORGANISM: Maize

<400> SEQUENCE: 4
atgggagaag cggccgcggc cgtggcggcg tcgaagaggg gcggcgggcc ggcgccgttc      60
ctgaccaaga cgcaccagat ggtggaggag cggggcacgg acgaggtgat ctcgtgggcg     120
gagcagggcc gctccttcgt ggtgtggaag cccgtggagc tggcgcgcga cctcctcccg     180
ctccacttca agcactgcaa cttctcctcc ttcgtccgcc agctcaacac ctacggtttc     240
cgaaaggtgg tgccgaccg tgggagttc gcgaacgaca acttccgtcg aggcgagcag      300
ggtctcctgt ccggcatccg ccgccgcaag tcaacggcgc tgcagatgtc caagtccgga     360
tccggcggca gcggcggcgt gaacgccacg ttccccccgc ctctgccccc tccgcctccc     420
gcgtcggcca ccacgtccgg cgtccacgag cgcagctcgt cggcgtc gtcgccaccg      480 cgggcgccg acctggccag cgagaacgag cagctcaaga aggacaacca cacgctgtcc     540
gccgagctgg cgcaggcgcg ccggcactgc gaggagctcc tgggcttcct ctcgcgcttc     600
ctcgacgtcc ggcagctcga cctccggctg ctcatgcagg aggacgtgcg agcggggca      660 agcgacgacg cgcacagcgc ccgcgcgcac gcagtggcca gccagctgga gcggcggc       720 ggcgaggagg ggaagagcgt gaagctgttc ggcgtactct taaaggacgc cgcgaggaag     780
```

| | |
|---|---|
| aggggccggt gcgaggaagc ggcggccagc gagcggccca tcaagatgat cagggtcggc | 840 |
| gagccgtggg tcggcgtccc gtcgtcgggc ccgggccggt gcggcggcga gaattaa | 897 |

<210> SEQ ID NO 5
<211> LENGTH: 7451
<212> TYPE: DNA
<213> ORGANISM: Maize

<400> SEQUENCE: 5

| | |
|---|---|
| ttgttgacta tatgtctgtt ttgttttgga agccgtaaca agggaccgca cagaacgata | 60 |
| cgactagtag gaactaggaa gagaacaggg aaggggtgg gaaagtgatg acaagttcgg | 120 |
| aattcctgca gccaaattcc ggtcctaggc ctcactaatt tggaccgaga gaaaaagcag | 180 |
| acacatatct cttccgtctt agcagtcaaa cgaaacacct agcagaacct tctctgtgcg | 240 |
| ccgttatccg tatccagttc gcttccgttc tcgcgtgaga tcagcaaaag aagctagcct | 300 |
| tgggtttgga ctgaccagct ggcctgcaac cgagcggatg gatgcgcgcc ggggtggct | 360 |
| ccaaaagtca gcatcttgtc gcgtggcaac ggtcagcgct ggcctcaatt ttctccgccc | 420 |
| cgcttctgtt tcagttggtg tgaggcgttt acatgggcga tcagatcacc gagttggaca | 480 |
| agcaattccc caaccaacaa cccttcgct tgcacgccag catggtggag ctatgcttac | 540 |
| agaatctccg gttcctgcac tggcagaact ttttttttt gggttcttaa gattatttt | 600 |
| aaaaactcta ccatttttc ccttcaaaat taacttggat cacgctcatt tctctagcca | 660 |
| cggtcaaatc acattgcctc gcaattcagt ctaacgcggt tagtcgattg ctatgattaa | 720 |
| aaaaatatat atttgggtag agatgtaaag aattttagtc agatcaaata cgttacgaaa | 780 |
| cttggttgaa tatagtatag tagttatatg ttctctatgc ttcggttagt tatttagtta | 840 |
| gaaatctcct gatatatact ccctccgttt ctttttattt gtcgctggat agtgtaattt | 900 |
| tacactatcc agcgacaaat aaaagaaac ggagggagta cttagtatat agtctaaaga | 960 |
| tggatagttg gaactgtcat ctgtgttgt ggcggttggt gtactgaact gaggatttgc | 1020 |
| tctagagtgg gcatccggta aagcactagt actttatagg tgctctcttt tgtttcgtgc | 1080 |
| acgtgttctc cgtacacaca cagagagaga cgatcgagat agaccatgat ccaagcattc | 1140 |
| catcggaaaa cttttaagca tacatccaac attctaggat taccagccac catcagtacc | 1200 |
| gtgcagcctg cacttaattc aaggttgtta tgaatggctg attttttatt tccatttatt | 1260 |
| cgcttatatt tatgaaaatt ggaactgcta actggaggaa tgaatgctat caagacacgc | 1320 |
| tagaaagaat atagatatta gagaatcctg aaaaaaaaa gataaacaca tccagtcatc | 1380 |
| tacttggcat aatataatca ttgttattag taacggtcat ccgatctgat ttataatgta | 1440 |
| atgactcgtt ccattatgtg ttattaaaga ccacctaaag taaactgctc cctccgttcc | 1500 |
| caaaataaaa catgttttac ctttttagtt gatttcatac aatagttaat acgtttgttt | 1560 |
| tatatatatg ttttttagatt catcatcgcc atccatttaa acattgacat aaaaaatgaa | 1620 |
| gagctaaaat taaacgactt aatgtttttag gatggaggga gtatatgtcg ttggagagtt | 1680 |
| ctagaaacgc cattctagac ctcttttgtac tacagttatg taaaaccata acattcaaac | 1740 |
| agagtctgag ctattttttga ctgatgacga gccctaagtc tatacataaa cctccaatat | 1800 |
| atatagacgg gttgagggtt caaagaccat tactactaag taatttgagt taagagaaag | 1860 |
| ttaattgcgc actagtagtt aaagacagct agatgaaatt agacatcaag tccgcctagt | 1920 |
| ataaatacag tagtacaatc cgcgtcgtca gtgtgacggc atggtcgacg cgccggccgg | 1980 |
| ggctgcgtgt gcgtgtcaag ctcggcccgg ccgatgattt cactttcccg gcgccgtttc | 2040 |

```
gtgtgccgat cgacgaaaaa gtccaagctt taatgatcgt ggtagccagc catcttgttc    2100
gcacctacct cgaatctgtt tttgttttgg cacggagaag aaatgaaatc aacggctgat    2160
gaaagtaact actagaagtt agtgataagt tacgataatt caaagtagct agtacgtcag    2220
cttattattc gatctgactg caagcatcat cgatatcgac ggcttgcaca cacggtagct    2280
agtttccttt tttttttcac ttttcgtttt caaagtccaa gagttttaaa tttgccgcag    2340
cgaagtttgg ctggcgcggc tgttgcgcgt acgtgtaggg aaaggaagg gatcagtcat    2400 cagtgagagc actcacgcgc aggcgggcgc ggcttcttcg gggtccgcgg aagcgagatg    2460
tggacaaatc gggggtgtgc cgcaccgcag tggagtgcga cgagcgctcc gagcacaagt    2520
ccgcgctcgc gcgcgcattt tccacgcgcc tttgggtggt ttactttctc tcccggcgac    2580
ggcgaggcag gcgcccgcca gcgtcacagg tggtgacgag gcattccggt gccgaggagg    2640
atccaaagga cagtcggttc gtcctggcgc ggtcgagacg ggccgggccc tcctccctcc    2700
tgtgcgtggg agccagccag ccagccagga gcggcgggcc ccgcttgggc gagcgacgaa    2760
ttttcgggcg ctttgactcg gctcggctca cggctcctgg atattggacg acaaagcggt    2820
ggaagcttct tatttggacc ggccgcgggc cggctgcaag gaagagcggc tgaaaggggt    2880
gggcgagctg actgctgagc atacgtaccc gcgcgaagaa gcagacggag gtcatcacgc    2940
tacccgcgcg tggccagtac cagacagact cctacctaca ctcagaaagc aagaagccca    3000
acgccgaaag caaccaccgc gctggtctct cgcctgtgcc gccctcgatc gcgcgtgaag    3060
agaagcccct cacttccgtc ctcctcctgt cctgtccagc taccccggcc ccgaccccga    3120
taaagcccgc cctttaaatc ggcggatcga ggcgatgagc gcctctcgcg acgccagggc    3180
ggagagctag ccggccggga gcccacacgc agctggaagc accagaccga tcgtgccggc    3240
cgagcggcgg cgcaggcgca ggcgcttaca tgggagtaga ggcgggcggg tgcggcggga    3300
gggcggtcgt caccgggttc tacgtctggg gctgggagtt cctcaccgcc ctccttctct    3360
tctcggccgc cgtcgccgcc gcagactcct actagcaagc taccaacctt ctttctttca    3420
ttcccttagg tagctcagcc gtacacacaa caacacacaa gtcatcagtt actagctagt    3480
tagtagccta tacaacacat acatacatac aaaggtgagt gaggttcgcg tgcaagcaga    3540
gccaatcgtg ccgatcgagc tatatacata gccggcggcg agggatggga gaagcggccg    3600
cggccgtggc ggcgtcgaag aggggcggcg ggccggcgcc gttcctgacc aagacgcacc    3660
agatggtgga ggagcggggc acggacgagg tgatctcgtg ggcggagcag ggccgctcct    3720
tcgtggtgtg gaagcccgtg gagctggcgc gcgacctcct cccgctccac ttcaagcact    3780
gcaacttctc ctccttcgtc cgccagctca cacctacgt gagtacacta cgccgccgct    3840
ccggccatca tctcttctac tacgatcgat gcaatatatc acctgtcgtc gtcgtttagt    3900
gattgcaaaa cacatacact tggtttccgt attaaattaa tcagctagct agctagatga    3960
tcgttctctg ctctatgatc tgttagttct gaagcatgtt gttgttttcg tctgtgctcg    4020
ataaattaag ctatgttatg tggtcgacga gcgagccttc caggcagcta ccgtaccgtc    4080
ttccaaggag tatatgcgtg tgagcgtgtc acggttcgta ggaaggagtg cgtcagtcat    4140
gacacatctc taccacccTT taattccttt cccacgcaaa gcatgcttgt cgtttcagag    4200
ctagctgaag aggaatgacc tgcgataaca cttgaagatt agggtgccgg tgcgggtctg    4260
aaattacacc tgtgggtacg atcgtgattt agatagacga cttcacggat gtgattacag    4320 gagtttttt tttctctac ctgatctaag gccctgtttg ggaacacagt ttttcaaac    4380
```

```
tgcagttttt caaatactaa agtatacttt agtcatgaca ttactacagt ttacaatgct    4440
tcagttttcg aatacaacag tattcaatac atcaaggtgt ttgggaaaaa ctttggttga    4500
gaccaatcag ccagagcggg accaagctgg cactctcttt acagagaaaa actttggctg    4560
agaccaaagt ttccaaaact gcaaaacaag tgcagtattt gcaatactac agtttagtat    4620
acagagattt cagatgagtt tccaaacacc tcaaagtata taataccaca gtattgctca    4680
atactacagt attgcttcaa tactgcagaa aaactttgtt cccaaacacc ccctaaactg    4740
ccatctctaa ctactatata tgtatagagc aaggtgcacg gggaaattga ataagcaaag    4800
caaatcaggt cggttgacac gccacggtat tgtagtggcg acagaagcat ggtattctat    4860
ggaacagtta aggccctgtt tgggaacaaa gttttgaaa accacagttt ttgaaatact    4920
atactatact ttagttatga caataccgta gtttataata ccgcagtttt gaaaactgag    4980
gtccagagct aagtttagaa tgccttaaaa caactatagt atttgcaata cttcagtttt    5040
gaaaacagag attttaccta gcttgccaaa caccattatg tatataatac tgcagtattt    5100
gagaatactg cagtattctt ccaaaactgc agaaaaactt tgttcccaaa caccccctaa    5160
gaagcttcgg atggacgagc ttttcagggc tagctcttct gcgtggccta caagaaggtt    5220
aatttagcta ggaattggat gctattagct gagcaagcaa tataatcatc caaggcatcc    5280
agcaagtata ctaatctttt gttgcctctt ccatctatta gctgggatac gaaatcgctc    5340
aagaaattga cttggaagtt aggatgatga tttaggccct gtttgtagtt tctccaacag    5400
ctagcttcat aatttgtttt tgttttttgg ctggatagta ttttccaaaa tagcttcatg    5460
gtatttggta aagcttcttc ttttttctc tctctcaagc caaggaaag tgatgcaggg    5520 atacgaatag ctgaaacacg agtagcttat tctagcgcag tcaaagattc acactgactt    5580
gggttcgttc tcactgaacc ttaatctatt aatcagaggg agagagagct agcttctcta    5640
aatcaatgtg tgaacagcta taaggcgtta tctgaccatg tgagcgacgt atggtggtca    5700
aagtagacag gcctgacgtg ttcatttcgg cgttttgttta gggactggct gaataggaca    5760
ctgtgtcgaa tgcagctctt gttctttttg ccgcattgga tacttacgtc gacggcgacc    5820
atggcgcatg cgcatccata tccatgcagg gtttccgaaa ggtggtgccg gaccggtggg    5880
agttcgcgaa cgacaacttc cgtcgaggcg agcagggtct cctgtccggc atccgccgcc    5940
gcaagtcaac ggcgctgcag atgtccaagt ccggatccgg cggcagcggc ggcgtgaacg    6000
ccacgttccc cccgcctctg ccccctccgc ctcccgcgtc ggccaccacg tccggcgtcc    6060
acgagcgcag ctcgtcgtcg gcgtcgtcgc caccgcgggc gcccgacctg gccagcgaga    6120
acgagcagct caagaaggac aaccacacgc tgtccgccga gctggcgcag gcgcgccggc    6180
actgcgagga gctcctgggc ttcctctcgc gcttcctcga cgtccggcag ctcgacctcc    6240
ggctgctcat gcaggaggac gtgcgagcgg gggcaagcga cgacggcgca cagcgccgcg    6300
cgcacgcagt ggccagccag ctggagcgcg cggcggcga ggaggggaag agcgtgaagc    6360
tgttcggcgt actcttaaag gacgccgcga ggaagagggg ccggtgcgag gaagcggcgg    6420
ccagcgagcg gcccatcaag atgatcaggg tcggcgagcc gtgggtcggc gtcccgtcgt    6480
cgggcccggg ccggtgcggc ggcgagaatt aactgtcatc caatgtgagg ttgatgacaa    6540
ggacagtttc atccatcata tcgagcaagt aacaaagcca gtgctgtggt aaaactgcaa    6600
agacagaaca caggacacag gagaaatata ggcgtaagca tgttaattaa gaattaatta    6660
tatatgggat gcttttgaag tagcaagatt ggaagtagag ataagtaaaa cgggctagaa    6720
gcagcgccca tgtgttcaga atggaaaatt agcgtttccg tgtgtgtgtt aagaaaaact    6780
```

```
tatatgcgct ttctgcgagc acggttgatt cttaagagcg acagcaaatg aaaggtgtat    6840
tattaattga aggtcacttg accacaaata ttacctatct catcatttcg ttatggcctt    6900
cacaggacga ggaagaaaga gaaggataga ctgtagagtt ctgtaaaaga ttctctaaat    6960
caataattta ggtaattaat ctaaaaactt ctagtctcaa caactcttta tatgaacttt    7020
ctaaatatag ctactcccca tctaatctca tttctatata catttgacaa ccatttacca    7080
actccataaa caaaaaaata atagttgcat taacgtaggt aatgaaagtg tgtgttgaca    7140
tttatgactt attttttaat gtgaatagat ttaaagtaag gccctgtttg tttcaactta    7200
tagattatat aatctagatt atagtttaga ttatataatc tggattattt gctctggatt    7260
aaataagcta ggtgctgctg tttgttagct cagattattt ggactcggct tattattcat    7320
atgcatacaa atacaataat acacttgatt gttttaattg tctggtgggt gagaacgctt    7380
atggataggt ggatggcaat tggaagtaat tttaatcaac ttgccatggg tagtgggtct    7440
ttcataaaaa a                                                          7451
```

<210> SEQ ID NO 6
<211> LENGTH: 299
<212> TYPE: PRT
<213> ORGANISM: Maize

<400> SEQUENCE: 6

```
Met Gly Glu Ala Ala Ser Ala Val Ala Ala Ser Lys Arg Gly Gly Gly
1               5                   10                  15

Gly Pro Ala Pro Phe Leu Thr Lys Thr His Gln Met Val Glu Glu Arg
            20                  25                  30

Gly Thr Asp Glu Val Ile Ser Trp Ala Glu Gln Gly Arg Ser Phe Val
        35                  40                  45

Val Trp Lys Pro Val Glu Leu Ala Arg Asp Leu Leu Pro Leu His Phe
    50                  55                  60

Lys His Cys Asn Phe Ser Ser Phe Val Arg Gln Leu Asn Thr Tyr Gly
65                  70                  75                  80

Phe Arg Lys Val Val Pro Asp Arg Trp Glu Phe Ala Asn Asp Asn Phe
                85                  90                  95

Arg Arg Gly Glu Gln Gly Leu Leu Ser Gly Ile Arg Arg Arg Lys Ser
            100                 105                 110

Thr Ala Leu Gln Met Ser Lys Ser Gly Ser Gly Ser Gly Val
        115                 120                 125

Asn Ala Thr Phe Pro Pro Pro Leu Pro Pro Pro Pro Ala Ser Ala
    130                 135                 140

Thr Thr Ser Gly Val His Glu Arg Ser Ser Ser Ala Ser Ser Pro
145                 150                 155                 160

Pro Arg Ala Pro Asp Leu Ala Ser Glu Asn Glu Gln Leu Lys Lys Asp
                165                 170                 175

Asn His Thr Leu Ser Val Glu Leu Ala Gln Ala Arg Arg His Cys Glu
            180                 185                 190

Glu Leu Leu Gly Phe Leu Ser Arg Phe Leu Asp Val Arg Gln Leu Asp
        195                 200                 205

Leu Arg Leu Leu Met Gln Glu Asp Val Arg Ala Gly Ala Ser Asp Asp
    210                 215                 220

Gly Ala Gln Arg Arg Ala His Ala Val Ala Ser Gln Leu Glu Arg Gly
225                 230                 235                 240

Gly Gly Glu Glu Gly Lys Ser Val Lys Leu Phe Gly Val Leu Leu Lys
```

```
                    245                 250                 255
Asp Ala Ala Arg Lys Arg Gly Arg Cys Glu Glu Ala Ala Ser Glu
                260                 265                 270

Arg Pro Ile Lys Met Ile Arg Val Gly Glu Pro Trp Val Gly Val Pro
            275                 280                 285

Ser Ser Gly Pro Gly Arg Cys Gly Gly Glu Asn
            290                 295

<210> SEQ ID NO 7
<211> LENGTH: 298
<212> TYPE: PRT
<213> ORGANISM: Maize

<400> SEQUENCE: 7

Met Gly Glu Ala Ala Ala Val Ala Ala Ser Lys Arg Gly Gly Gly
1               5                   10                  15

Pro Ala Pro Phe Leu Thr Lys Thr His Gln Met Val Glu Glu Arg Gly
            20                  25                  30

Thr Asp Glu Val Ile Ser Trp Ala Glu Gln Gly Arg Ser Phe Val Val
            35                  40                  45

Trp Lys Pro Val Glu Leu Ala Arg Asp Leu Leu Pro Leu His Phe Lys
    50                  55                  60

His Cys Asn Phe Ser Ser Phe Val Arg Gln Leu Asn Thr Tyr Gly Phe
65                  70                  75                  80

Arg Lys Val Val Pro Asp Arg Trp Glu Phe Ala Asn Asp Asn Phe Arg
                85                  90                  95

Arg Gly Glu Gln Gly Leu Leu Ser Gly Ile Arg Arg Lys Ser Thr
            100                 105                 110

Ala Leu Gln Met Ser Lys Ser Gly Ser Gly Gly Ser Gly Val Asn
            115                 120                 125

Ala Thr Phe Pro Pro Pro Leu Pro Pro Pro Pro Ala Ser Ala Thr
            130                 135                 140

Thr Ser Gly Val His Glu Arg Ser Ser Ser Ala Ser Ser Pro Pro
145                 150                 155                 160

Arg Ala Pro Asp Leu Ala Ser Glu Asn Glu Gln Leu Lys Lys Asp Asn
                165                 170                 175

His Thr Leu Ser Ala Glu Leu Ala Gln Ala Arg Arg His Cys Glu Glu
            180                 185                 190

Leu Leu Gly Phe Leu Ser Arg Phe Leu Asp Val Arg Gln Leu Asp Leu
            195                 200                 205

Arg Leu Leu Met Gln Glu Asp Val Arg Ala Gly Ala Ser Asp Asp Gly
            210                 215                 220

Ala Gln Arg Arg Ala His Ala Val Ala Ser Gln Leu Glu Arg Gly Gly
225                 230                 235                 240

Gly Glu Glu Gly Lys Ser Val Lys Leu Phe Gly Val Leu Leu Lys Asp
                245                 250                 255

Ala Ala Arg Lys Arg Gly Arg Cys Glu Ala Ala Ser Glu Arg
            260                 265                 270

Pro Ile Lys Met Ile Arg Val Gly Glu Pro Trp Val Gly Val Pro Ser
            275                 280                 285

Ser Gly Pro Gly Arg Cys Gly Gly Glu Asn
            290                 295

<210> SEQ ID NO 8
<211> LENGTH: 22
```

```
<212> TYPE: DNA
<213> ORGANISM: Artificial Sequence
<220> FEATURE:
<223> OTHER INFORMATION: Ubip-F

<400> SEQUENCE: 8
ttttagccct gccttcatac gc                                              22

<210> SEQ ID NO 9
<211> LENGTH: 22
<212> TYPE: DNA
<213> ORGANISM: Artificial Sequence
<220> FEATURE:
<223> OTHER INFORMATION: Nos-R

<400> SEQUENCE: 9
agaccggcaa caggattcaa tc                                              22

<210> SEQ ID NO 10
<211> LENGTH: 21
<212> TYPE: DNA
<213> ORGANISM: Artificial Sequence
<220> FEATURE:
<223> OTHER INFORMATION: ZmHsf21-Q-F

<400> SEQUENCE: 10
ctccttcgtg gtgtggaagc c                                               21

<210> SEQ ID NO 11
<211> LENGTH: 23
<212> TYPE: DNA
<213> ORGANISM: Artificial Sequence
<220> FEATURE:
<223> OTHER INFORMATION: ZmHsf21-Q-R

<400> SEQUENCE: 11
acagcgtgtg gttgtccttc ttg                                             23

<210> SEQ ID NO 12
<211> LENGTH: 20
<212> TYPE: DNA
<213> ORGANISM: Artificial Sequence
<220> FEATURE:
<223> OTHER INFORMATION: ZmUBQ-Q-F

<400> SEQUENCE: 12
ctggtgccct ctccatatgg                                                 20

<210> SEQ ID NO 13
<211> LENGTH: 23
<212> TYPE: DNA
<213> ORGANISM: Artificial Sequence
<220> FEATURE:
<223> OTHER INFORMATION: ZmUBQ-Q-R

<400> SEQUENCE: 13
caacactgac acgactcatg aca                                             23
```

MAIZE ZmHsf21 GENE AND USE THEREOF

CROSS-REFERENCE TO RELATED APPLICATIONS

This application is a U.S. national stage application, filed under 35 U.S.C. § 371(c), based on International Patent Application No. PCT/CN2020/106580, filed on Aug. 3, 2020, which claims priority to Chinese Patent Application No. 201910775329.8 filed on Aug. 21, 2019.

TECHNICAL FIELD

The present invention relates to the field of plant genetic engineering, and in particular, to ZmHsf21 genes, proteins encoded thereby, and use thereof in plant breeding.

SEQUENCE LISTING

The instant application contains a Sequence Listing which has been filed electronically in ASCII format and is hereby incorporated by reference in its entirety. Said ASCII copy, created on Dec. 26, 2023 and having a size of 23,240 bytes, is named 132173_00302_SL.txt.

BACKGROUND OF THE INVENTION

Under high temperature stress, organisms will make a heat shock response, and generate a heat shock protein (HSP), which, as a molecular chaperone, maintains normal functions of other proteins at high temperature, so as to improve the heat resistance of organisms. Studies have shown that HSP is ubiquitous in numerous organisms from bacteria to higher eukaryotes, and plays an important role in almost all living cells. The transcription of a heat shock protein gene is regulated by a heat shock transcription factor (HSF). In a heat shock response, heat-activated HSF can recognize a heat shock element (HSE) present in the promoter region upstream of the HSP gene, thereby inducing the expression of HSP.

The plant HSF system is far more diverse and complex than other organisms. There are many types of HSFs in all the plants that have been studied, for example, there are 21 HSFs in *Arabidopsis;* 18 HSFs have been found in tobacco; more than 16 HSFs have been found in tomato; 23 HSFs have been found in rice; and up to 34 HSFs have been found in soybeans. Studies have shown that plant HSF plays an important role in growth and development (Kotak et al., 2007a; Liu et al., 2011) and in response to adversity stress (Kotak et al., 2007b), and is induced by multiple adversities, e.g., high temperatures (Baniwal et al., 2004), drought (Sakuma et al., 2006), salt (Li et al., 2013), oxidation (Davletova et al., 2005), strong sunlight (Nishizawa et al., 2006), etc.

The plant HSF mainly includes a DNA binding domain (DBD), an oligomerization domain (OD), a nuclear localization signal (NLS), C-terminal heptad repeats (HR-C), and an activation domain (AD). According to the DNA binding domains and the comparison of their polymerization regions, plant HSF proteins can be divided into classes A and B. Class A HSF (HsfA) is mainly responsible for regulating the expression of heat shock genes. Class B HSF (HsfB) does not have a transcriptional activation activity due to the absence of an activation domain. However, HsfB has a DNA binding activity, and thus may work together with HsfA. For instance, in tomatoes, HsfB1, as a coactivator of HsfA1, has the function of assisting activation, and can increase the efficiency of HsfA1 recognizing a heat shock gene promoter, thereby improving the transcription of heat shock genes (Bharti et al., 2004; Hahn et al., 2011). Specifically, at room temperature, the HSF protein in a tomato binds to Hsp70 or Hsp90 in a monomeric form and is in an inactive state. Under stress conditions such as high temperature, the aggregated or misfolded protein competitively binds with molecular chaperones such as Hsp70 and Hsp90, thereby releasing an HSF protein, so that HsfA1, HsfB1, and HAC1 are bound to form a trimer having an activation activity, which finally binds to HSE at the upstream of the Hsp gene promoter and induces the transcription of the Hsp gene. When the HSP protein accumulates to some extent or the stress is relieved, the HSP protein binds to Hsf again, to inhibit the activity of the Hsf, and turn off the transcription of Hsp by Hsf (Scharf et al., 2012).

Notwithstanding the in-deptin studies on the HSF functions of tomatoes and *Arabidopsis*, the study on HSF of maize as a major crop is still in its infancy stage. The present invention is the first to study the HsfB1 gene (i.e., ZmHsf21 gene) in maize and explore its important role in plant breeding, especially in increasing yield and improving plant disease resistance (such as stalk rot).

SUMMARY OF THE INVENTION

In one aspect, the present invention provides an isolated nucleic acid molecule, comprising a nucleotide sequence selected from the group consisting of:
  (1) a sequence set forth in SEQ ID NOs:1-5;
  (2) a sequence hybridizing to a complementary sequence of the sequence set forth in SEQ ID NOs:1-5 under stringent conditions;
  (3) a sequence having at least 85% identity to the sequence set forth in SEQ ID NOs:1-5, wherein a protein that is encoded by the sequence has functions of improving plant yield and/or resistance to stalk rot; and
  (4) a sequence obtained from the sequence set forth in SEQ ID NOs:1-5 by insertion, deletion, or substitution of one or more nucleotides, wherein a protein that is encoded by the sequence has functions of improving plant yield and/or resistance to stalk rot; and
  a heterologous promoter operably linked to the nucleotide sequence.

In another aspect, the present invention provides an isolated nucleic acid molecule, comprising a nucleotide sequence selected from the group consisting of:
  (1) a nucleotide sequence encoding the sequence set forth in SEQ ID NO:6 or 7;
  (2) a nucleotide sequence encoding a polypeptide having at least 85% identity to the sequence set forth in SEQ ID NO:6 or 7, wherein a protein that is encoded by the nucleotide sequence has functions of improving plant yield and/or resistance to stalk rot; and
  (3) a nucleotide sequence encoding a polypeptide obtained from the sequence set forth in SEQ ID NO:6 or 7 by insertion, deletion, or substitution of one or more amino acids, wherein a protein that is encoded by the nucleotide sequence has functions of improving plant yield and/or resistance to stalk rot; and
  a heterologous promoter operably linked to the nucleotide sequence.

In another aspect, the present invention provides an isolated polypeptide, comprising a sequence selected from the group consisting of:

(1) a sequence set forth in SEQ ID NO:6 or 7; and
(2) a polypeptide obtained from the sequence set forth in SEQ ID NO:6 or 7 by insertion, deletion, or substitution of one or more amino acids, and having functions of improving plant yield and/or resistance to stalk rot.

In another aspect, the present invention provides an expression vector, comprising the nucleic acid molecule as set forth above.

In another aspect, the present invention provides a host cell, comprising the nucleic acid molecule or the expression vector as set forth above.

In another aspect, the present invention provides a transgenic plant, comprising the nucleic acid molecule or the expression vector as set forth above.

In one embodiment, compared with a control plant, the transgenic plant has an increased yield or an improved resistance to stalk rot.

In another embodiment, the transgenic plant is selected from the group consisting of: maize, sorghum, soybean, wheat, rice, cotton, *Brassica campestris*, barley, millet, tomato, sunflower, potato, peanut, sweat potato, cassava, oat, beet, tobacco, *Arabidopsis*, and sugar cane.

In one aspect, the present invention provides use of the nucleic acid molecule or the expression vector or the protein as set forth above in increasing plant yield or improving stalk rot resistance of a plant.

In one aspect, the present invention provides a method for increasing plant yield, comprising the steps of:
(1) introducing the nucleic acid molecule or the expression vector as set forth above into the plant; and
(2) cultivating the plant, wherein compared with a control plant, the plant has an increased yield.

In one embodiment, the plant is selected from the group consisting of: maize, sorghum, soybean, wheat, rice, cotton, *Brassica campestris*, barley, millet, tomato, sunflower, potato, peanut, sweat potato, cassava, oat, beet, tobacco, *Arabidopsis*, and sugar cane.

In one aspect, the present invention provides a method for improving stalk rot resistance of a plant, comprising the steps of:
(1) introducing the nucleic acid molecule or the expression vector as set forth above into the plant; and
(2) cultivating the plant, wherein compared with a control plant, the plant has improved resistance to stalk rot.

In one embodiment, the plant is selected from the group consisting of: maize, sorghum, soybean, wheat, rice, cotton, *Brassica campestris*, barley, millet, tomato, sunflower, potato, peanut, sweat potato, cassava, oat, beet, tobacco, *Arabidopsis*, and sugar cane.

DETAILED DESCRIPTION OF THE INVENTION

Figure 1:
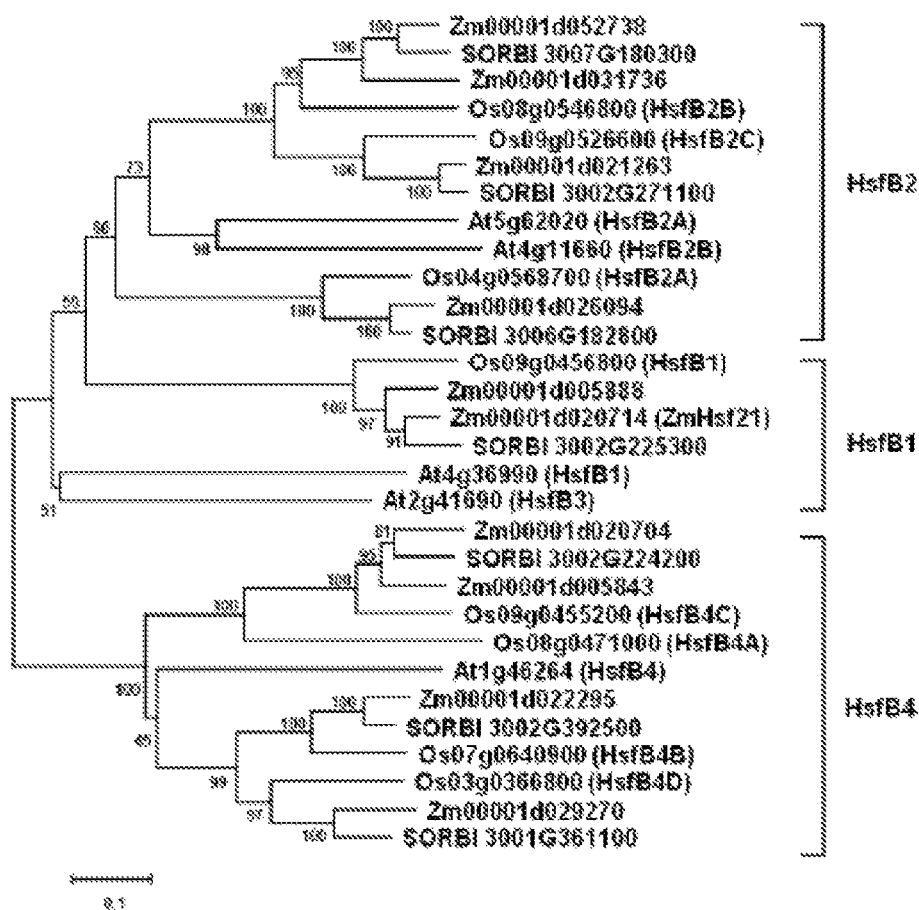
FIG. 1: phylogenetic trees of HsfB genes of maize, rice, sorghum, and *Arabidopsis*.

The following definitions and methods are provided to better define the present invention and guide those skilled in the art to implement the present invention. Unless otherwise specified, all technologies and terms used herein have the same meanings as commonly understood by the technicians in the field to which the present invention belongs. Unless otherwise particularly indicated, the techniques applied and encompassed herein are standard methods well known to those skilled in the art. The materials, methods, and examples are for illustrative purposes only, and do not restrict the scope of protection for the present invention in any way.

As used herein, "plant" includes a whole plant, a plant part, a plant cell, and progenies thereof. The plant part includes, but is not limited to, leaves, stalks, tubers, roots, flowers (including, for example, bracts, sepals, petals, stamens, carpels, anthers, ovules, etc.), fruits, embryos, endosperms, seeds, pollen, meristalks, calluses, protoplasts, microspores, etc. In one embodiment, the plant part or plant cell of the present invention is renewable. In another embodiment, the plant part or plant cell of the present invention is non-renewable.

The plant species available in the present invention generally encompass higher plant species suitable for transgenic technology, including monocotyledonous plants and dicotyledonous plants. Specifically, plants suitable for the present invention are selected from the group consisting of: maize, sorghum, soybean, wheat, rice, cotton, *Brassica campestris*, barley, millet, tomato, sunflower, potato, peanut, sweat potato, cassava, oat, beet, tobacco, *Arabidopsis*, and sugar cane. Preferably, the plant suitable for the present invention is maize or rice.

As used herein, "transgenic plant" refers to a plant containing a heterologous polynucleotide. The transgenic plant includes plants regenerated from initially transformed plant cells and transgenic progenies from subsequent generations or hybrids of the transgenic plants.

As used herein, "control plant" means a plant free of recombinant DNA that confers enhanced traits. Control plants are used to identify and select transgenic plants with enhanced traits. A suitable control plant may be a non-transgenic plant used to generate a parent line of a transgenic plant, for example, a wild-type plant lacking recombinant DNA. Suitable control plants may also be transgenic plants containing recombinant DNA conferring other traits, for example, a transgenic plant with enhanced herbicide tolerance.

As used herein, the term "stringent conditions" or "stringent hybridization conditions" includes conditions under which a probe will hybridize to a target sequence with higher detectability (e.g., at least 2 times higher than background) than other sequences. Stringent conditions will vary depending on different sequences and circumstances. By controlling the stringency of hybridization and/or washing regulation, a target sequence that is up to 100% complementary to the probe can be detected. Alternatively, the stringency can also be regulated so that there are some mismatches in the sequence, thereby detecting the target sequences with lower identity. The hybridization specificity depends on the washing step after hybridization.

The key factors are the salt concentration and temperature in the washing solution. As appropriate, both the temperature and the salt concentration can be changed, or the temperature or salt concentration remains unchanged while the other variable is changed. Appropriate stringent conditions that promote DNA hybridization are known to those skilled in the art. Exemplary lower stringent conditions include the following: hybridization at 37° C. in a buffer solution containing 30-35% formamide, 1M NaCl, and 1% SDS, and washing with 1-2×SSC (sodium chloride/sodium citrate) at 50° C.-55° C. Exemplary moderately stringent conditions include the following: hybridization at 37° C. in a buffer solution containing 40-45% formamide, 1M NaCl, and 1% SDS, and washing with 0.5-1×SSC at 55° C.-60° C. Exemplary highly stringent conditions include the following: hybridization at 37° C. in a buffer solution containing 50% formamide, 1M NaCl, and 1% SDS, and washing with 0.1×SSC at 60° C.-65° C. As for a detailed description of nucleic acid hybridization, see Sambrook et al., 1989, and Haymes et al., "Nucleic Acid Hybridization, A Practical Approach", IRL Press, Washington, DC (1985), and "Current Protocols in Molecular Biology", John Wiley & Sons, NY (1989), 6.3.1-6.3.6.

As used herein, "percent identity" or "% identity" refers to the number of matches between two polynucleotide sequences or protein sequences in an alignment window, where the polynucleotide sequences or protein sequences in the alignment window may include additions or deletions (i.e., vacancies) in comparison to the reference sequences to achieve optimal alignment of the two sequences. Methods for polynucleotide sequences and protein sequences alignment are well known to those skilled in the art, for example, by software, e.g., Clustal, Bestfit, Blast, Fasta, etc. The percent identity is determined by calculating the number of positions of the same nucleic acid or amino acid in the two sequences, dividing it by the full length of the reference sequence (excluding vacancies introduced into the reference sequence during alignment), and multiplying the result by 100. The reference sequence may be, for example, SEQ ID NO:1, SEQ ID NO:2, or SEQ ID NO:3. In one embodiment, the nucleotide sequence of the present invention has at least 85%, 86%, 87%, 88%, 89%, 90%, 91%, 92%, 93%, 94%, 95%, 96%, 97%, 98%, 98.5%, 99%, 99.5% or 100% identity to the sequence set forth in SEQ ID NO:1 or 2. In one embodiment, the polypeptide sequence of the present invention has at least 85%, 86%, 87%, 88%, 89%, 90%, 91%, 92%, 93%, 94%, 95%, 96%, 97%, 98%, 98.5%, 99%, 99.5% or 100% identity to the sequence set forth in SEQ ID NO:3.

In one embodiment, the nucleic acid sequence of the present invention includes sequences obtained from the sequences set forth in SEQ ID NOs:1-5 by insertion, deletion, and/or substitution of one or more nucleotides. In another embodiment, the nucleic acid sequence of the present invention includes a sequence obtained from the sequence set forth in SEQ ID NO:6 or 7 by insertion, deletion, and/or substitution of one or more amino acids. Such insertion, deletion, and/or substitution do not impair the functions of the original sequence (which, for example, means herein that the functions of improving plant yield and/or resistance to stalk rot are still kept). Those skilled in the art know the methods for introducing insertion, deletion and/or substitution of one or more nucleotides/amino acids into the original sequence while preserving the biological function of the original sequence, e.g., choosing to make such insertion, deletion and/or substitution in the non-conservative regions. For example, due to the degeneracy of genetic codons, those skilled in the art can modify nucleotides by "silent mutation" without changing the polypeptides encoded by the nucleotides. Alternatively, those skilled in the art can replace one amino acid in a protein with another amino acid of similar properties through "conservative substitution" without affecting the biological function of the protein. Conservative substitution may occur in the following groups: (1) acidic (negatively charged) amino acids, such as aspartic acid and glutamic acid; (2) basic (positively charged) amino acids, such as arginine, histidine and lysine; (3) neutral polar amino acids, such as glycine, serine, threonine, cysteine, tyrosine, asparagine and glutamine; and (4) neutral non-polar (hydrophobic) amino acids, such as alanine, leucine, isoleucine, valine, proline, phenylalanine, tryptophan and methionine. As for the conservative substitution for amino acids in natural proteins or polypeptides, it can be selected from other members of the group to which the natural amino acids belong. For instance, the group of amino acids having aliphatic side chains includes glycine, alanine, valine, leucine, and isoleucine; the group of amino acids having aliphatic-hydroxyl side chains includes serine and threonine; the group of amino acids having amide-containing side chains includes asparagine and glutamine; the group of amino acids having aromatic side chains includes phenylalanine, tyrosine and tryptophan; the group of amino acids having basic side chains includes lysine, arginine and histidine; and the group of amino acids having sulfur-containing side chains includes cysteine and methionine. The group of conservatively-substituted natural amino acids includes valine-leucine, valine-isoleucine, phenylalanine-tyrosine, lysine-arginine, alanine-valine, and aspartic acid-glutamic acid, and asparagine-glutamine.

As used herein, "host cell" refers to a cell that contains an expression vector and supports the expression vector to replicate and/or express. The host cell may be a prokaryotic cell (such as *E. coli* cell or *Agrobacterium tumefaciens* cell) or a eukaryotic cell (such as yeast, insect, plant or animal cell). The host cell is preferably a monocotyledonous or dicotyledonous plant cell, including, but not limited to, cells from maize, sorghum, soybean, wheat, rice, cotton, *Brassica campestris*, barley, millet, tomato, sunflower, potato, peanut, sweat potato, cassava, oat, beet, tobacco, *Arabidopsis*, or sugar cane. More preferably, the host cell is a maize cell.

As used herein, "introduction" of a nucleic acid molecule or an expression vector into a plant or a plant cell means transfection, transformation, transduction, or incorporation of the nucleic acid molecule or the expression vector into a host cell, so that the nucleic acid molecule can autonomously replicate or express in the host cell. In one embodiment, the introduced nucleic acid molecule is integrated into the cell genome (e.g., chromosome, plasmid, plastid, or mitochondrial DNA). In another embodiment, the introduced nucleic acid molecule is not integrated into the cell genome.

As used herein, the term "promoter" refers generally to a DNA molecule that is involved in recognition and binding of RNA polymerase II and other proteins (trans-acting transcription factors) to initiate transcription. A promoter may be initially isolated from the 5'untranslated region (5'UTR) of a genomic copy of a gene. Alternatively, a promoter may be a synthetically produced or manipulated DNA molecule. A promoter may also be chimeric, namely, a promoter produced through the fusion of two or more heterologous DNA molecules. The plant promoter includes promoter DNA obtained from plants, plant viruses, fungi, and bacteria such as *Agrobacterium*.

As used herein, "heterologous promoter" means that the promoter and the gene of interest are derived from different species, or if they are derived from the same species, the promoter and/or the gene of interest are substantially changed relative to its natural form.

As used herein, "operably linked" refers to a functional connection between a first sequence (e.g., a promoter) and a second sequence (e.g., a gene of interest), wherein the promoter sequence initiates and mediates the transcription of the second sequence. Generally, two operably linked sequences are adjacent.

As used herein, "stalk rot" refers to a serious disease caused by fungi or bacteria, which mainly harms the basal part of stalk or the underground axial and lateral roots. The diseased part is dark brown at the beginning, and then pervasive in the basal part of stalk, causing the cortex to rot and the aboveground leaves to be yellow and wilted. The whole plant dies later and exhibits dropping ears, and dark brown sclerotia of uneven sizes are often formed on the surface of the diseased part. Stalk rot is common in tomatoes, potatoes, maize and other plants. Maize stalk rot, also known as bacterial wilt and stalk rot, is one of the major diseases in the maize production. The maize stalk rot has a relatively higher incidence and seriously affects the yield and quality of maize, resulting in a production decline, even up to 50% or more.

The inventors are the first to discover that the ZmHsf21 gene exhibits significant effects of increasing plant yield and improving stalk rot resistance of a plant, which provides a new and valuable approach to maize breeding.

Description of sequences of ZmHsf21 gene

| SEQ ID NO | Maize Variety | Type | Length |
|---|---|---|---|
| SEQ ID NO: 1 | Zheng 58 | cDNA | 1535 bp |
| SEQ ID NO: 2 | B73 | cDNA | 1671 bp |
| SEQ ID NO: 3 | Zheng 58 | CDS | 900 bp |
| SEQ ID NO: 4 | B73 | CDS | 897 bp |
| SEQ ID NO: 5 | B73 | Genomic DNA | 7451 bp |
| SEQ ID NO: 6 | Zheng 58 | Protein | 299 aa |
| SEQ ID NO: 7 | B73 | Protein | 298 aa |

In the above sequences, SEQ ID NO:1 and SEQ ID NO:2 have 98% sequence identity; SEQ ID NO:3 and SEQ ID NO:4 have 99% sequence identity; and SEQ ID NO:6 and SEQ ID NO:7 have 99% sequence identity.

Specific Embodiments

Unless otherwise specified, all of the examples below are implemented under conventional experimental conditions (e.g., see Sambrook J & Russell D W, Molecular cloning: a laboratory manual, 2001), or according to manufacturers' instructions.

Example 1. Construction of ZmHsf21 Gene Overexpression Vector

Figure 2:
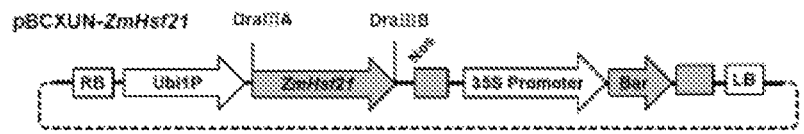
FIG. 2: a recombinant expression vector pBXCUN-ZmHsf21.

Firstly, in accordance with the manufacturer's instructions, the Magnetic Beads Plant Total RNA Extraction Kit (BioTeke Corporation, No. AU3402) was used to extract RNA from the leaves at V4 stage of the maize variety Zheng 58, and then the High-Capacity cDNA Reverse Transcription Kit (Thermo Scientific Corporation, No. 4368814) was used to reversely transcribe the RNA into cDNA and to construct a whole genome cDNA library. Thereafter, the cDNA library was sequenced. With reference to the published B73 sequence and gene annotations, and through bioinformatics methods, a plasmid containing a complete cDNA sequence of the ZmHsf21 gene was obtained by screening, and a cDNA sequence (SEQ ID NO:1) of the ZmHsf21 gene was obtained by enzyme digestion with a restriction enzyme Quick cut SfiI (TaKaRa Corporation, No. 1637). The purified ZmHsf21 cDNA sequence was ligated with a pBCXUN vector (NCBI GenBank: FJ905215, see, e.g., Plant Physiol. 150 (3), 1111-1121 (2009)) to obtain a recombinant expression vector pBCXUN-ZmHsf21 (FIG. 2). The recombinant expression vector was used to transform *E. coli*. Positive clones were screened, and sequenced to determine that they contained a complete ZmHsf21 gene.

Example 2. Preparation of ZmHsf21 Transgenic Maize

A recombinant expression vector pBXCUN-ZmHsf21 was introduced into an *Agrobacterium* EHA105 strain to obtain a recombinant bacterium. Afterwards, the recombinant bacterium was introduced into a maize inbred line B73-329 by the *Agrobacterium*-mediated transformation to obtain a transgenic plant at T0 generation.

Leaves of seedlings of the transgenic plant at T0 generation were picked up, from which the genomic DNA was extracted. The genomic DNA was taken as a template to perform PCR amplification using a primer Ubip-F (targeting 5' end of an Ubi1P promoter of the recombinant expression vector pBXCUN-ZmHsf21) and a primer Nos-R (targeting 3' end of a Nos terminator of the recombinant expression vector pBXCUN-Zm Hsf21). The genomic DNA of leaves of seedlings of the maize inbred line B73-329 served as a negative control, and the plasmid of the recombinant expression vector pBXCUN-ZmHsf21 served as a positive control.

```
Ubip-F: 5'-TTTTAGCCCTGCCTTCATACGC-3';

Nos-R: 5'-AGACCGGCAACAGGATTCAATC-3'.
```

The product obtained by PCR amplification was detected by agarose gel electrophoresis. The result indicated that a single band of 1725 bp was amplified by each of the transgenic plant and the plasmid, while the amplification did not generate a corresponding band on the parent B73-329. It indicated the ZmHsf21 was successfully introduced into the transgenic plant.

The identified transgenic plants at T0 generation were selfed to obtain transgenic plants at T1 progeny. The transgenic plants at T1 progeny were then selfed to obtain transgenic plants at T2 progeny. The transgenic plants at T2 progeny were then selfed to obtain transgenic plants at T3 progeny. Positive transgenic plants at each generation were identified by the PCR amplification as set out above, and then selfed. Four representative homozygous transgenic lines (namely, 0098341009, 0098341022, 0098341084, and 0098341087) at T3 generation were selected for subsequent function analysis experiments.

Example 3. Detection of Expression Level of ZmHsf21 Gene

In this example, four representative homozygous transgenic lines (namely, 0098341009, 0098341022, 0098341084, and 0098341087) at T3 generation and the maize inbred line B73-329(WT) were plants to be detected.

Firstly, in accordance with the manufacturer's instructions, the Magnetic Beads Plant Total RNA Extraction Kit (BioTeke Corporation, No. AU3402) was used to extract RNA from the leaves at V4 stage of the plant to be tested, and then the High-Capacity cDNA Reverse Transcription Kit (Thermo Scientific Corporation, No. 4368814) was used to reversely transcribe the RNA into cDNA.

Thereafter, in an SYBR Premix Ex Taq™ II (Tli RNaseH Plus) kit (Takara Corporation, No. RR820A), cDNA was taken as a template to perform real-time fluorescent quantitative PCR amplification using specific primers ZmHsf21-Q-F (5'-CTCCTTCGTGGTGTGGAAGCC-3' (SEQ ID NO:10)) and ZmHsf21-Q-R (5'-ACAGCGTGTGGTTGTCCTTCTTG-3' (SEQ ID NO:11)), so as to detect the expression level of the ZmHsf21 gene. The cDNA of the maize inbred line B73-329(WT) was used as a control. The maize UBQ gene was used as an internal reference gene, which was detected by primers ZmUBQ-Q-F: 5'-CTGGTGCCCTCTCCATATGG-3' (SEQ ID NO:12) and ZmUBQ-Q-R: 5'-CAACACTGACACGACT-CATGACA-3' (SEQ ID NO:13). The reaction process for the fluorescent quantitative PCR amplification was listed in Table 1 below.

TABLE 1

| Steps | Temperature | Time | Cycles |
|---|---|---|---|
| 1: Pre-denaturation | 95° C. | 30 sec | 1 |
| 2: PCR reaction | 95° C. | 5 sec | 40 |
|  | 60° C. | 34 sec |  |
| 3: Melt Curve | 95° C. | 15 sec | 1 |
|  | 60° C. | 1 min |  |
|  | 95° C. | 15 sec |  |

Figure 3:
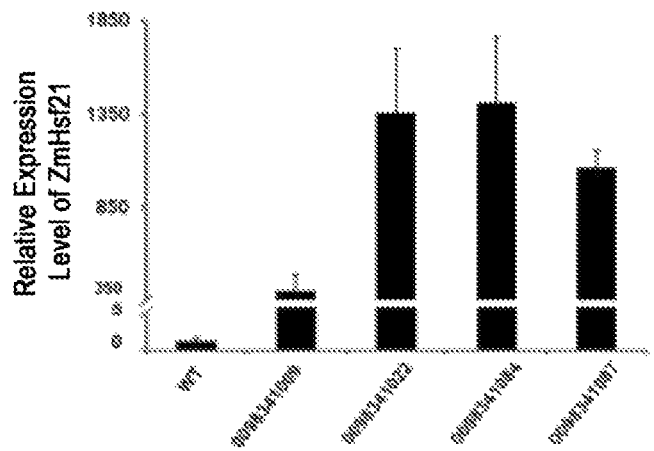
FIG. 3: relative expression of the ZmHsf21 gene in leaves of wild-type and transgenic plants.

The results of the fluorescent quantitative PCR were as shown in FIG. 3. As can be seen from FIG. 3, the expression levels of ZmHsf21 in the transgenic lines 0098341009, 0098341022, 0098341084 and 0098341087 were all significantly higher than that in the maize inbred line B73-329 (WT), wherein the expression levels in the transgenic lines 0098341084 and 0098341022 even reached to about 1350 times that in the wild-type maize B73-329, and the lower expression level of 0098341009 among the transgenic lines was also up to about 350 times that in the B73-329. Those results showed that the ZmHsf21 gene had been successfully expressed in the homozygous transgenic lines 0098341009, 0098341022, 0098341084 and 0098341087 at T3 generation.

Example 4. Analysis of Yield of Transgenic Maize

The four homozygous transgenic lines at T3 generation were used as male parents and crossed with T13 to obtain four transgenic homozygous lines F1 (namely, F1-1009, F1-1022, F1-1084 and F1-1087), and overexpression of the ZmHsf21 gene therein was confirmed in accordance with the fluorescent quantitative PCR method as described above. In the meantime, F1-B73 obtained by crossing B73-329 with T13 was used as a control plant. F1-B73, F1-1009, F1-1022, F1-1084 and F1-1087 were planted in six locations (Gongzhuling, Shangzhuang, Baotou, Zhuozhou, Anyang, and Yinchuan, 2 repeats for each location) in 2016 and in eight locations (Gongzhuling, Baotou, Zhuozhou, Anyang, Kaifeng, and Yinchuan, 3 repeats for each location) in 2017, respectively. After harvest, each line was measured to determine its field traits, including yield, ear length, ear diameter, barren-tip length, rows per ear, kernels per row, plot kernel weight, grain moisture, hundred kernel weight, etc.

Figure 4:
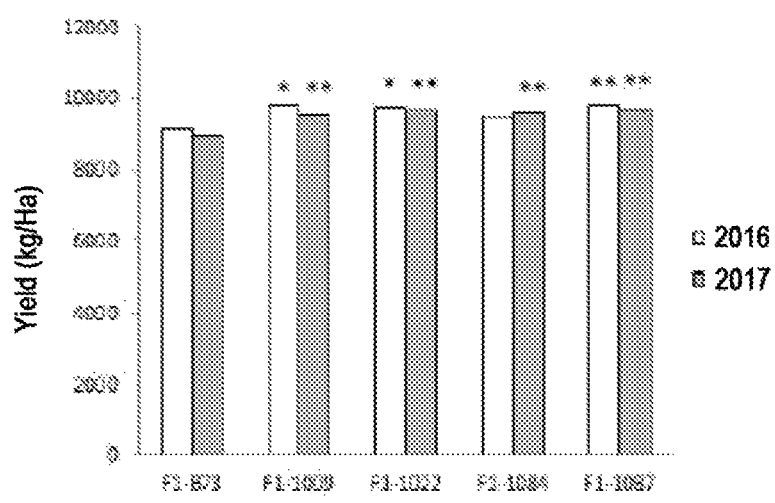
FIG. 4: yields of wild-type and transgenic plants in 2016 and 2017; analysis by a Dunnett's test, * $p \leq 0.05$; ** $p \leq 0.01$.

FIG. 4 showed the results of comparison between the yield of the transgenic maize and that of the control plant. As shown in FIG. 4, the yields of the four transgenic lines F1-1009, F1-1022, F1-1084 and F1-1087 in per unit yield assays of the two years were stably higher than the yields of the control groups. Specifically, compared with the yields of the control plants F1-B73, the yields of F1-1009, F1-1022 and F1-1087 in 2016 were increased by 7.6%, 6.6% and 7.5% respectively and reached a significant level; and the yields of F1-1009, F1-1022, F1-1084 and F1-1087 in 2017 were increased by 6.6%, 7.9%, 7.2% and 8.3%, and all reached an extremely significant level. The above results indicate that the ZmHsf21 gene exhibits significant overexpression and stably increases the maize yield.

Figure 5:
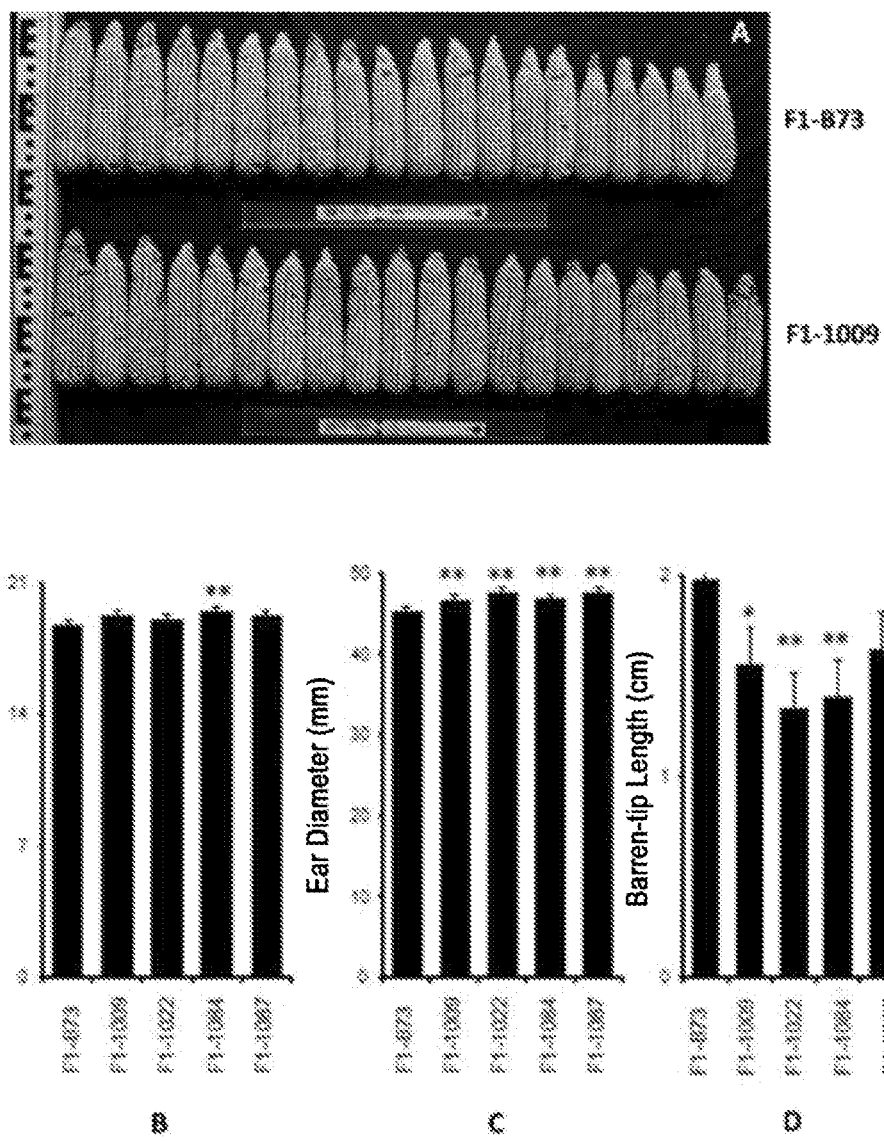
FIG. 5: comparisons of quality of ears (A), ear length (B), ear diameter (C) and barren-tip length (D) of the control plant and the transgenic plant; analysis by a Dunnett's test, * $p \leq 0.05$; ** $p \leq 0.01$.

FIG. 5 showed the comparison results between the transgenic maize and the control plant in terms of the quality, ear length, ear diameter and barren-tip length. As shown in FIG. 5, the ear lengths of F1-1009, F1-1022, F1-1084 and F1-1087 were increased by 2.36%, 1.62%, 3.66% and 2.35% respectively in comparison to the control plant (see FIG. 5B); the ear diameters were increased by 3.19%, 5.41%, 3.40% and 5.24% respectively in comparison to the control plant and all reached an extremely significant level (see FIG. 5C); meanwhile, the barren-tip lengths were reduced by 21.5%, 32.6%, 29.5% and 17.5% respectively in comparison to the control plant (see FIGS. 5A and 5D). The results above indicate that the overexpression of the ZmHsf21 gene also significantly improves traits such as the ear length, ear diameter and barren-tip length.

Example 5. Analysis of Stalk Rot Resistance of Transgenic Maize

Materials used in this example were as same as those used in Example 4, namely, transgenic maize lines F1-1009, F1-1022, F1-1084 and F1-1087. F1-B73 was used as a control plant.

Figure 6:
FIG. 6: results of the control plant and the transgenic plant infected by pathogens of stalk rot. A: field performance of the control plant and the transgenic plant infected by pathogens of stalk rot; B: longitudinal section of stalks of representative control plant and transgenic plant; C: comparison of incidence rate of stalks of the control plant and the transgenic plant; analysis by a Dunnett's test, * $p \leq 0.05$; ** $p \leq 0.01$.
Figure 6:
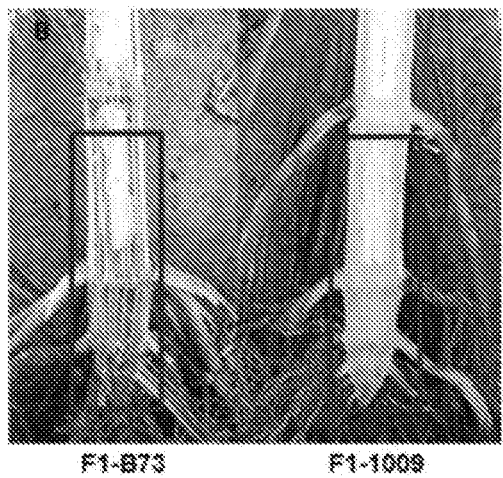
Figure 6:
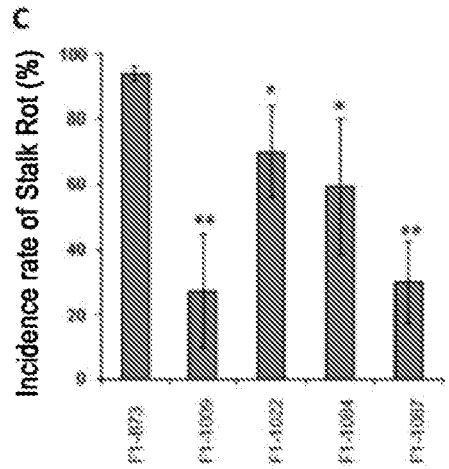

By artificial inoculation, the roots of respective plants were inoculated with the pathogens of stalk rot (*Fusarium graminearum*, inoculation quantity of 50 g/plant) at the flowering stage. 45 days after the inoculation, the field performance of the plants was observed to count the incidence rate of stalks, and the stalks of the representative plants were longitudinally sectioned to observe the phenotypes. The results were shown in FIG. 6.

As shown FIG. 6A, after infected with the pathogens of stalk rot, a lot of leaves of the control plants were yellowed and withered and the whole plants were even dead, while the transgenic maize plants were healthier without serious yellowing leaves or death of the whole plants. As shown in FIG. 6B, the longitudinal section of stalks of the representative plants indicated that a hollow phenomenon occurred in stalks of the control plants as a result of the stalk rot, and on the contrary, the transgenic maize plants were basically kept healthy. The statistical results of the incidence rate of stalks further demonstrated that the incidence rate of the transgenic maize plants were significantly lower than that of the control plants (see FIG. 6C).

The results above indicate that the transgenic maize lines of the present invention exhibit good resistance to stalk rot, and that the overexpression of the ZmHsf21 gene can improve the stalk rot resistance of maize.

It should be understandable to those skilled in the art that the technologies disclosed in the Examples are the best

REFERENCES

1. Baniwal S K, Bharti K, Chan K Y et al. Heat stress response in plants: a complex game with chaperones and more than twenty heat stress transcription factors. J Biosci, 2004, 29(4): 471-487.
2. Bharti K, von Koskull-Doring P, Bharti S et al. Tomato heat stress transcription factor HsfB1 represents a novel type of general transcription coactivator with a histone-like motif interacting with the plant CREB binding protein ortholog HAC1. Plant Cell, 2004, 16(6): 1521-1535.
3. Davletova S, Rizhsky L, Liang H et al. Cytosolic ascorbate peroxidase 1 is a central component of the reactive oxygen gene network of Arabidopsis. Plant Cell, 2005, 17(1): 268-281.
4. Hahn A, Bublak D, Schleiff E, Scharf K D, Crosstalk between Hsp90 and Hsp70 chaperones and heat stress transcription factors in tomato. Plant Cell, 2011, 23(2) 741-755.
5. Kotak S, Larkindale J, Lee U et al. Complexity of the heat stress response in plants. Curr Opin Plant Biol, 2007b, 10(3): 310-316.
6. Kotak S, Vierling E, Baumlein H et al. A novel transcriptional cascade regulating expression of heat stress proteins during seed development of Arabidopsis. Plant Cell, 2007a, 19(1): 182-195.
7. Li Z, Zhang L, Wang A et al. Ectopic overexpression of SlHsfA3, a heat stress transcription factor from tomato, cofers increased thermotolerance and salt hypersensitivity in germination in transgenic Arabidopsis. PLoS ONE, 2013, 8(1): e54880.
8. Liu H C, Liao H T, Chang Y Y, The role of class A1 heat shock factors (HSFA1s) in response to heat and other stresses in Arabidopsis. Plant Cell Environ, 2011, 34(5): 738-751.
9. Mueller D, Wise K. Corn disease loss estimates from the United States and Ontario, Canada-2013. Purdue Extension Publication, 2014, BP-96-13-W.
10. Nishizawa A, Yabuta Y, Yoshida E et al. Arabidopsis heat shock transcription factor A2 as a key regulator in response to several types of environmental stress. Plant J, 2006, 48(4): 535-547.
11. Sakuma Y, Maruyama K, Qin F et al. Dual function of an Arabidopsis transcription factor DREB2A in water-stress-responsive and heat-stress-responsive gene expression. Proc Natl Acad Sci USA, 2006, 103(49): 18822-18827.
12. Scharf K D, Berberich T, Ebersberger I et al. The plant heat stress transcription factor (Hsf) family: Structure, function and evolution. Biochimica et Biophysica Acta, 2012, 1819(2): 104-119.
13. Xia J H, Fang Z D. Research for Pathogen of Maize Bacterial Stalk Rot Journal of Plant Protection. 1962, 1: 1-14.

What is claimed is:

1. An isolated nucleic acid molecule, comprising a nucleotide sequence selected from the group consisting of
   (1) a sequence set forth in SEQ ID NOs: 1 and 5 and
   (2) a sequence having at least 99% or 99.5% identity to the sequence set forth in SEQ ID NOs: 1 and 5, wherein a protein that is encoded by the sequence has functions of improving plant yield and/or resistance to stalk rot; and a heterologous promoter operably linked to the nucleotide sequence.

2. An expression vector, comprising the nucleic acid molecule according to claim 1.

3. A host cell, comprising the nucleic acid molecule according to claim 1.

4. A transgenic plant, comprising the nucleic acid molecule according to claim 1.

5. The transgenic plant according to claim 4, wherein the transgenic plant is a crop plant.

6. The transgenic plant according to claim 4, wherein the transgenic plant is selected from the group consisting of: maize, sorghum, soybean, wheat, rice, cotton, *Brassica campestris*, barley, millet, tomato, sunflower, potato, peanut, sweat potato, cassava, oat, beet, tobacco, *Arabidopsis*, and sugar cane.

7. A method for increasing plant yield, comprising the steps of:
   (1) introducing the nucleic acid molecule according to claim 1 into the plant; and
   (2) cultivating the plant, wherein compared with a control plant, the plant has an increased yield.

8. The method according to claim 7, wherein the plant is selected from the group consisting of: maize, sorghum, soybean, wheat, rice, cotton, *Brassica campestris*, barley, millet, tomato, sunflower, potato, peanut, sweat potato, cassava, oat, beet, tobacco, *Arabidopsis*, and sugar cane.

9. A method for improving stalk rot resistance of a plant, comprising the steps of:
   (1) introducing the nucleic acid molecule according to claim 1 into the plant; and
   (2) cultivating the plant, wherein compared with a control plant, the plant has improved resistance to stalk rot.

10. The method according to claim 9, wherein the plant is selected from the group consisting of: maize, sorghum, soybean, wheat, rice, cotton, *Brassica campestris*, barley, millet, tomato, sunflower, potato, peanut, sweat potato, cassava, oat, beet, tobacco, *Arabidopsis*, and sugar cane.

* * * * *